(12) United States Patent
Jetti et al.

(10) Patent No.: US 11,466,031 B2
(45) Date of Patent: Oct. 11, 2022

(54) POLYMORPHIC FORMS OF BICTEGRAVIR AND ITS SODIUM SALT

(71) Applicant: Mylan Laboratories Limited, Hyderabad (IN)

(72) Inventors: Ramakoteswara Rao Jetti, Hyderabad (IN); Daveedu Bhatraju, Hyderabad (IN); Subramanyam Dandala, Hyderabad (IN); Aggi Ramireddy Bommareddy, Hyderabad (IN); Rajendar Reddy Mulamalla, Hyderabad (IN); Sridhar Tailor, Hyderabad (IN); Sureshbabu Jayachandra, Hyderabad (IN)

(73) Assignee: Mylan Laboratories Limited

( * ) Notice: Subject to any disclaimer, the term of this patent is extended or adjusted under 35 U.S.C. 154(b) by 0 days.

(21) Appl. No.: 17/050,531

(22) PCT Filed: Apr. 25, 2019

(86) PCT No.: PCT/IN2019/050335
§ 371 (c)(1),
(2) Date: Oct. 26, 2020

(87) PCT Pub. No.: WO2019/207602
PCT Pub. Date: Oct. 31, 2019

(65) Prior Publication Data
US 2021/0355137 A1    Nov. 18, 2021

(30) Foreign Application Priority Data

Apr. 26, 2018 (IN) .............................. 201841015814
Jun. 4, 2018 (IN) .............................. 201841020810
Sep. 10, 2018 (IN) .............................. 201841034008

(51) Int. Cl.
*C07D 498/22*    (2006.01)

(52) U.S. Cl.
CPC ........ *C07D 498/22* (2013.01); *C07B 2200/13* (2013.01)

(58) Field of Classification Search
None
See application file for complete search history.

(56) References Cited

PUBLICATIONS

PCT International Search Report on Patentability PCT/IN2019/050335 dated Oct. 31, 2019.
Written Opinion of the International Searching Authority for PCT/IN2019/050335 dated Oct. 31, 2019.

*Primary Examiner* — Samantha L Shterengarts (57) ABSTRACT

The present disclosure provides crystalline forms of bictegravir, amorphous bictegravir sodium, amorphous solid dispersion of bictegravir sodium with pharmaceutically acceptable carrier and processes for the preparation thereof.

5 Claims, 6 Drawing Sheets

Figure 1: Powder X-ray diffraction pattern of crystalline bictegravir Form M1

Figure 2: Powder X-ray diffraction pattern of crystalline bictegravir Form M2

Figure 3: Powder X-ray diffraction pattern of crystalline bictegravir Form M3

Figure 4: Powder X-ray diffraction pattern of crystalline bictegravir Form M4

Figure 5: Powder X-ray diffraction pattern of crystalline bictegravir Form M5

Figure 6: Powder X-ray diffraction pattern of amorphous bictegravir sodium

POLYMORPHIC FORMS OF BICTEGRAVIR AND ITS SODIUM SALT

CROSS-REFERENCE TO RELATED APPLICATIONS

This application is a U.S. national stage application under 35 U.S.C. § 371 of International Application No. PCT/IN2019/050335, filed Apr. 25, 2019, which claims the benefit of Indian Provisional Patent Application No. IN201841015814 filed on Apr. 26, 2018; Indian Provisional Patent Application No. IN201841020810 filed on Jun. 4, 2018; Indian Provisional Patent Application No. IN201841034008 filed on Sep. 10, 2018.

FIELD OF THE INVENTION

The present disclosure encompasses crystalline forms of bictegravir, amorphous form of bictegravir sodium, amorphous solid dispersion of bictegravir sodium and processes for their production and pharmaceutical compositions thereof.

BACKGROUND OF THE INVENTION

Bictegravir (formerly known as GS-9883) also referred to as bictegravir free acid is a human immunodeficiency virus type 1 (HIV-1) integrase strand transfer inhibitor that was discovered by Gilead Sciences.

Bictegravir sodium is approved as part of a single tablet regimen in combination with tenofovir alafenamide (TAF) and emtricitabine (FTC) for the treatment of HIV-1 infection under the brand name of BIKTARVY®, marketed by Gilead Sciences. Bictegravir sodium is chemically known as (2R, 5S,13aR)-2,5-Methanopyrido[1',2':4,5]pyrazino[2,1-b][1,3]oxazepine-10-carboxamide, 2,3,4,5,7,9, 13,13a-octahydro-8-hydroxy-7,9-dioxo-N-[(2,4,6-trifluorophenyl)methyl]-, sodium salt (1:1), having the structure below:

Formula-I

Bictegravir is disclosed in U.S. Pat. No. 9,216,996 B2, which is hereby incorporated by reference.

The inventors of the present disclosure have developed novel crystalline forms of bictegravir, amorphous bictegravir sodium, amorphous solid dispersion of bictegravir sodium with pharmaceutically acceptable carriers and a process for the preparation.

SUMMARY OF THE INVENTION

Figure 1:
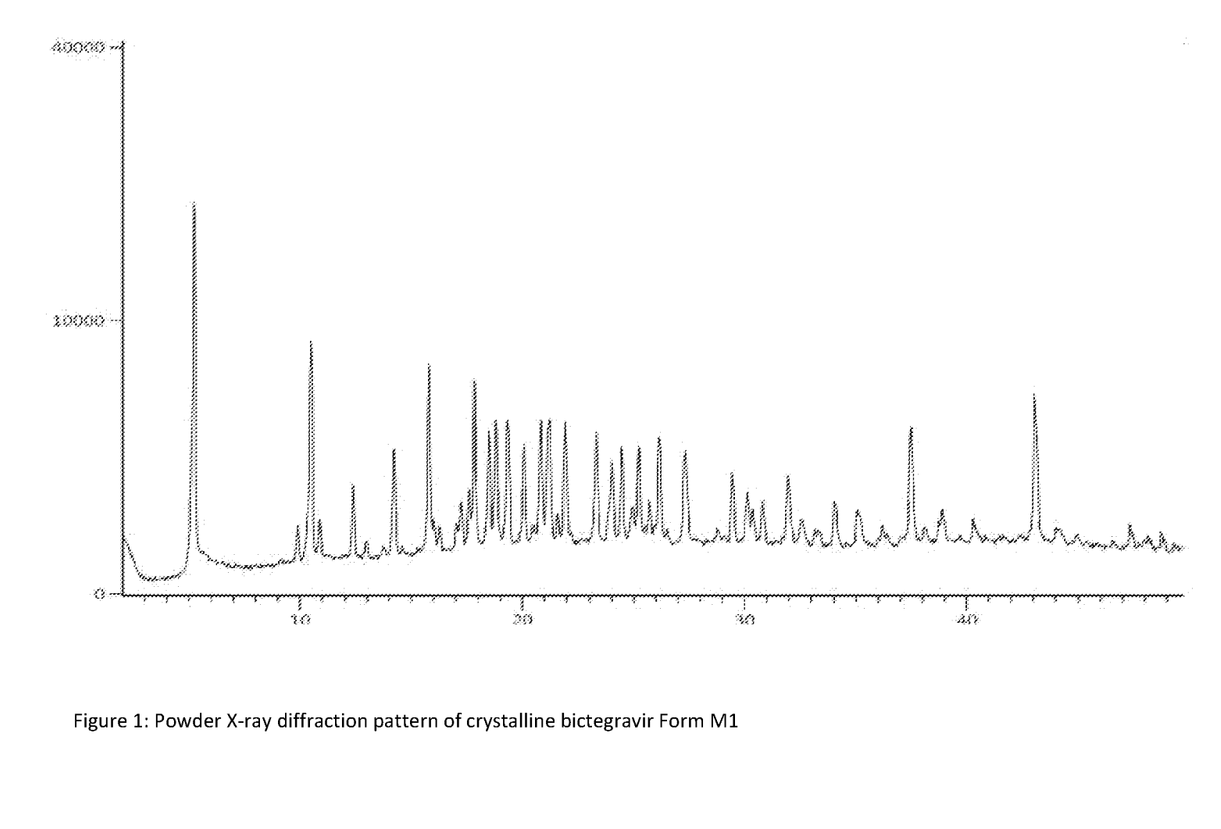
FIG. 1 is an X-ray powder diffractogram of crystalline bictegravir Form M1.

In one aspect, the present invention provides crystalline bictegravir Form M1, which may be characterized by a PXRD pattern having significant peaks at 2θ angles of 5.23, 10.50, 15.79 and 17.84±0.2°. Crystalline bictegravir Form M1 may also be characterized by a PXRD pattern as shown in FIG. 1.

In another aspect, the present invention provides a process for the preparation of crystalline bictegravir Form M1. In one embodiment, crystalline bictegravir Form M1 may be prepared by a process comprising the steps of:
a) dissolving bictegravir sodium and fumaric acid in a mixture of water and organic solvent at elevated temperature;
b) cooling the reaction mass to 20-35° C.;
c) stirring the reaction mass to form the precipitation; and
d) isolating crystalline bictegravir Form M1.

Figure 2:
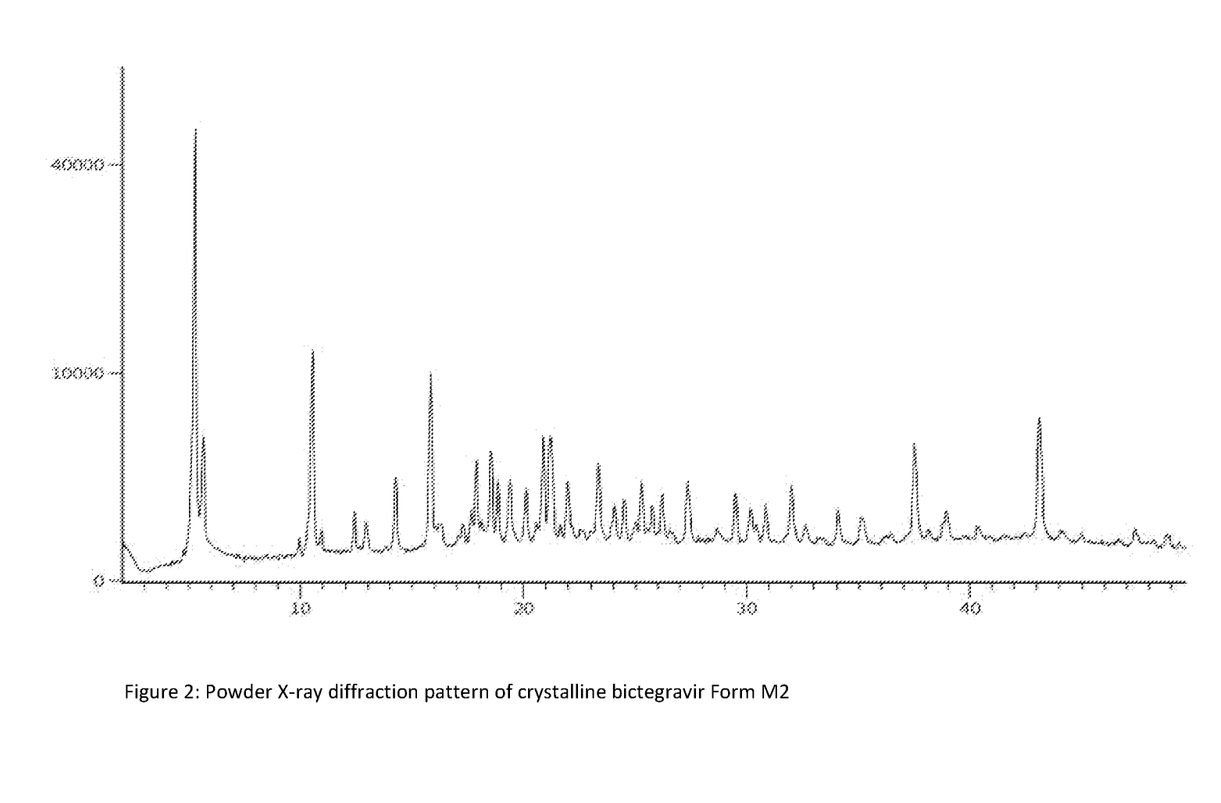
FIG. 2 is an X-ray powder diffractogram of crystalline bictegravir Form M2.

In one aspect, the present invention provides crystalline bictegravir Form M2, which may be characterized by a PXRD pattern having significant peaks at 2θ angles of 5.27, 10.54, 14.25, and 15.83±0.2°. Crystalline bictegravir Form M2 may also be characterized by a PXRD pattern as shown in FIG. 2.

In another aspect, the present invention provides a process for the preparation of crystalline bictegravir Form M2 comprising the steps of:
a) dissolving bictegravir sodium and succinic acid in a mixture of water and organic solvent at elevated temperature;
b) cooling the reaction mass to 20-35° C.;
c) stirring the reaction mass to form the precipitation; and
d) isolating crystalline bictegravir Form M2.

Figure 3:
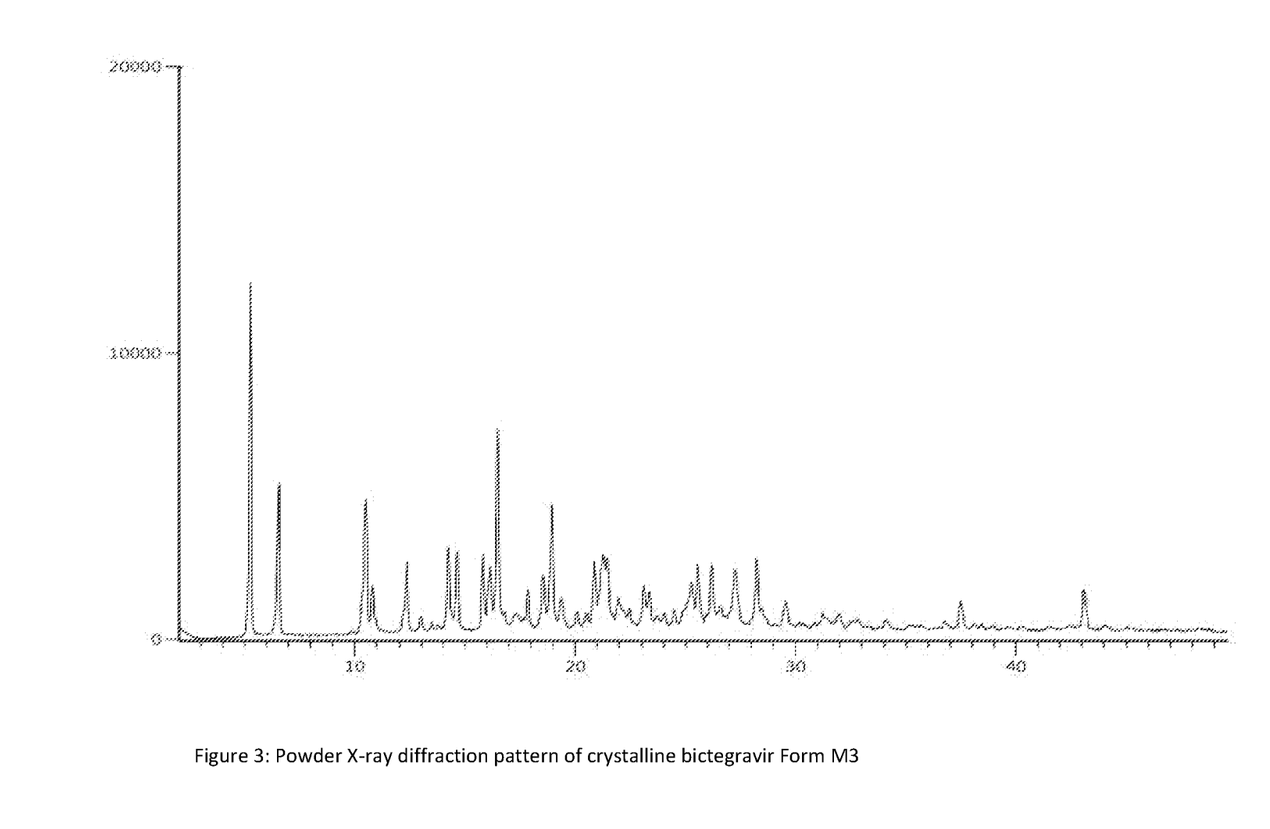
FIG. 3 is an X-ray powder diffractogram of crystalline bictegravir Form M3.

In another aspect, the present invention provides crystalline bictegravir Form M3, which may be characterized by a PXRD pattern having significant peaks at 2θ angles of 5.25, 10.50, 14.22 and 16.47±0.2°. Crystalline bictegravir Form M3 may also be characterized by a PXRD pattern as shown in FIG. 3.

In another aspect, the present invention provides a process for the preparation of crystalline bictegravir Form M3 comprising the steps of:
a) dissolving bictegravir sodium and oxalic acid in a mixture of water and polar aprotic solvent at elevated temperature;
b) cooling the reaction mass to 20-35° C.;
c) stirring the reaction mass to form the precipitation; and
d) isolating crystalline bictegravir Form M3.

Figure 4:
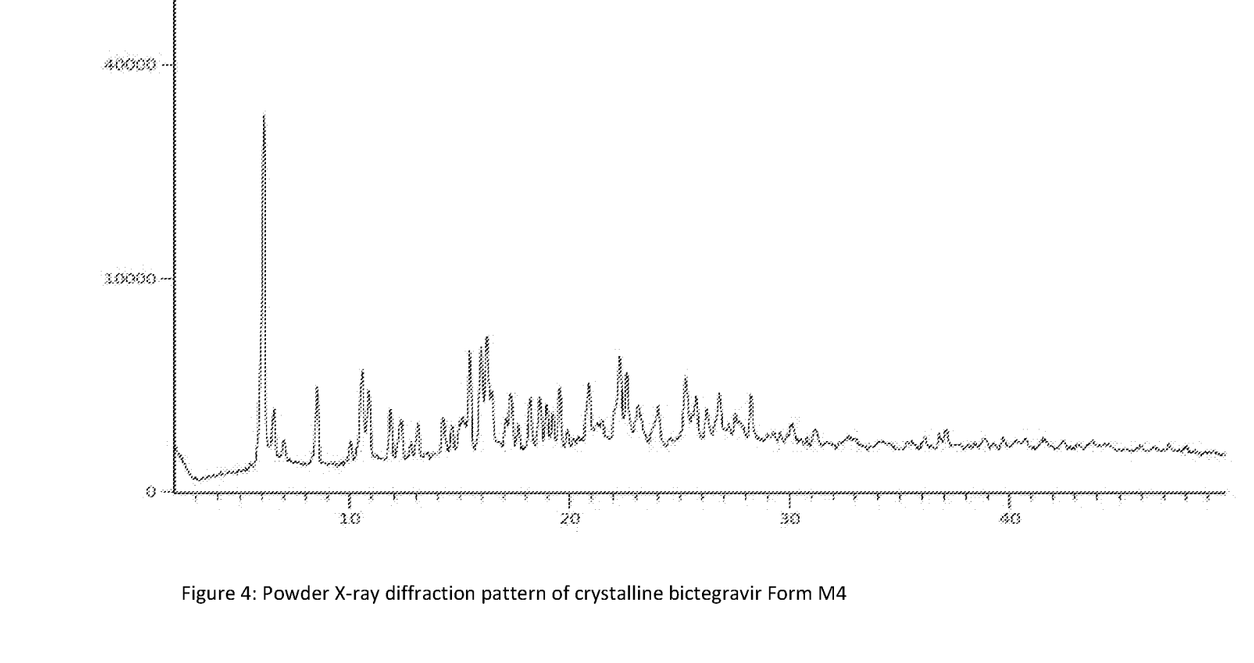
FIG. 4 is an X-ray powder diffractogram of crystalline bictegravir Form M4.

In another aspect, the present invention provides crystalline bictegravir Form M4, which may be characterized by a PXRD pattern having significant peaks at 2θ angles of 10.96, 16.98, 20.15, 22.16 and 26.01±0.2°. Crystalline bictegravir Form M4 may also be characterized by a PXRD pattern as shown in FIG. 4.

Other aspect of the present invention is to provide a process for the preparation of crystalline bictegravir Form M4 comprising the steps of:
a) dissolving bictegravir sodium and oxalic acid in a mixture of water and alcohol solvent at elevated temperature;
b) cooling the reaction mass to 20-35° C.;
c) stirring the reaction mass to form the precipitation; and
d) isolating crystalline bictegravir Form M4.

Figure 5:
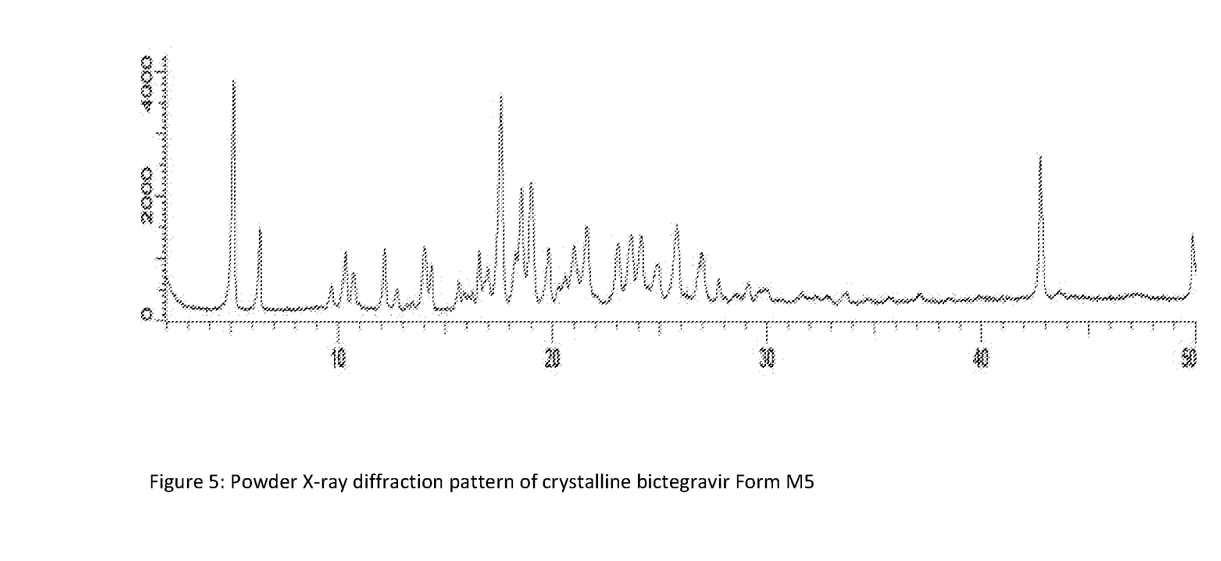
FIG. 5 is an X-ray powder diffractogram of crystalline bictegravir Form M5.

In another aspect, the present invention provides crystalline bictegravir Form M5, which may be characterized by a PXRD pattern having significant peaks at 2θ angles of 5.12, 6.33, 10.35 and 17.59±0.2°. Crystalline bictegravir Form M5 may also be characterized by a PXRD pattern as shown in FIG. 5.

Another aspect of the present invention is to provide a process for the preparation of crystalline bictegravir Form M5, comprising drying the crystalline bictegravir Form M3 at 160-200° C.

Figure 6:
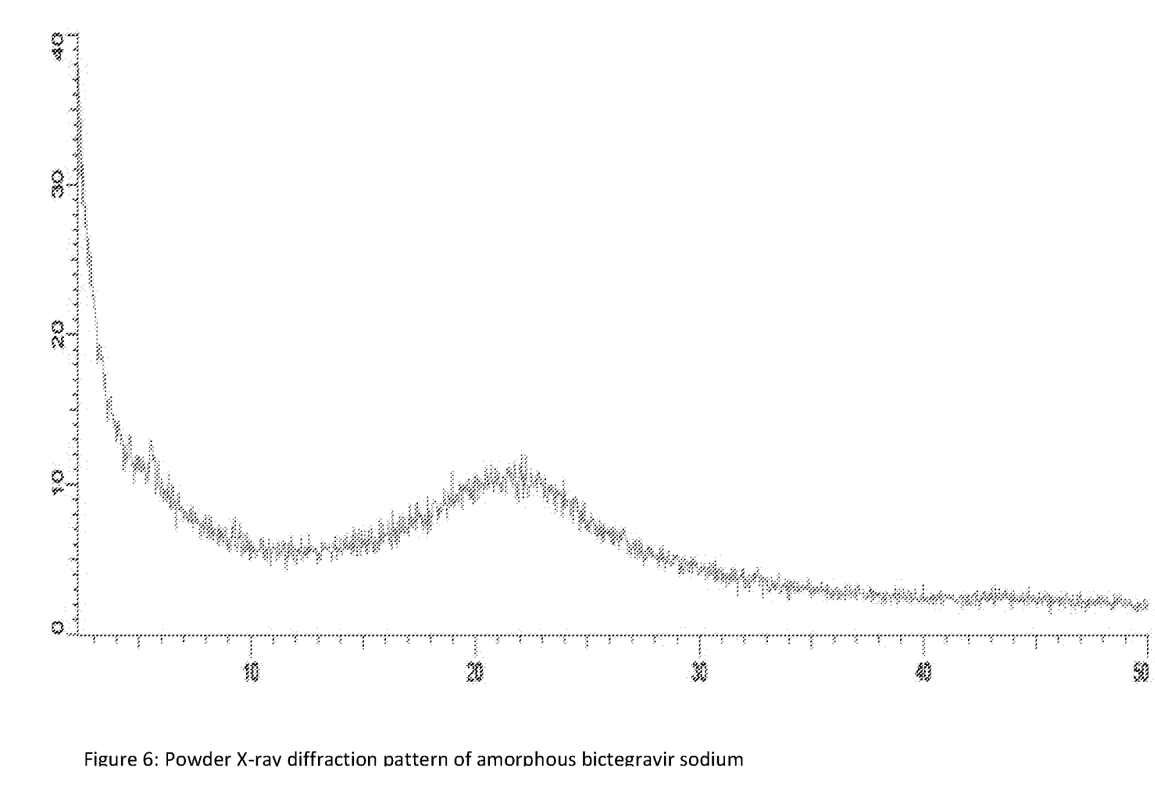
FIG. 6 is an X-ray powder diffractogram of amorphous bictegravir sodium.

In another aspect, the present invention provides amorphous bictegravir sodium. Amorphous bictegravir sodium may also be characterized by a PXRD pattern as shown in FIG. 6.

Another aspect of the present invention is to provide a process for the preparation of amorphous bictegravir sodium, which comprises:
a) dissolving bictegravir sodium in a solvent; and
b) removing the solvent and isolating the amorphous bictegravir sodium.

In another aspect, the present invention provides amorphous solid dispersion of bictegravir sodium with pharmaceutically acceptable carriers.

Another aspect of the present invention is to provide a process for the preparation of amorphous solid dispersion of bictegravir sodium with pharmaceutically acceptable carriers, which comprises:
a) dissolving bictegravir sodium in a solvent;
b) adding pharmaceutically acceptable carrier to the solution obtained in step (a);
c) removing the solvent and isolating the amorphous solid dispersion of bictegravir sodium.

Another aspect of the present invention is to provide a process for the preparation of amorphous solid dispersion of bictegravir sodium with pharmaceutically acceptable carriers, which comprises:
a) dissolving bictegravir sodium and pharmaceutically acceptable carrier in a solvent; and
b) removing the solvent and isolating the amorphous solid dispersion of bictegravir sodium.

BRIEF DESCRIPTION OF THE FIGURES

Further aspects of the present disclosure together with additional features contributing thereto and advantages accruing there from will be apparent from the following description of embodiments of the disclosure which are shown in the accompanying drawing figures wherein.

DETAILED DESCRIPTION OF THE DISCLOSURE

The present disclosure relates to crystalline forms of bictegravir, amorphous bictegravir sodium and amorphous solid dispersion of bictegravir sodium with pharmaceutically acceptable carriers. The present disclosure also relates to process for the preparation of crystalline forms of bictegravir, amorphous bictegravir sodium and amorphous solid dispersion of bictegravir sodium.

Within the context of the present disclosure, the term "about" when modifying a temperature measurement is meant to mean the recited temperature plus or minus five degrees. Within the context of the present disclosure, the term "about" when modifying an absolute measurement, such as time, mass, or volume, means the recited value plus or minus 10% of the value.

Within the context of the present disclosure, the term "elevated temperature" means the temperature above 35° C. and it is depending on the water/organic solvent ratio and the concentration of bictegravir sodium/organic acid.

The crystalline forms of bictegravir disclosed herein may be characterized by X-ray powder diffraction pattern (PXRD). Samples of each polymorph were analyzed on a BRUKER D-8 Discover powder diffractometer equipped with goniometer of θ/2θ configuration and Lynx Eye detector. The Cu-anode X-ray tube was operated at 40 kV and 30 mA. The experiments were conducted over the 2θ range of 2.0°-50.0°, 0.030° step size and 0.4 seconds step time.

In one aspect, the present invention provides crystalline bictegravir Form M1.

Within the context of the present invention, crystalline bictegravir Form M1 may be characterized by a PXRD pattern having significant peaks at 2θ angle positions at about 5.23, 10.50, 15.79 and 17.84±0.2°. In another embodiment, crystalline bictegravir Form M1 may be characterized by a PXRD pattern having significant peaks at 2θ angle positions at about 5.23, 10.50, 12.38, 13.76, 14.21, 15.79 and 17.84±0.2°. In yet another embodiments, crystalline bictegravir Form M1 may be characterized by a PXRD pattern having significant peaks at 2θ angle positions at about 5.23, 9.88, 10.50, 10.89, 12.38, 12.98, 13.76, 14.21, 15.79, 16.27, 17.24, 17.59, 17.84, 18.49, 18.80, 19.35, 20.07, 20.48, 20.82, 21.22, 21.59, 21.92, 23.32, 24.03, 24.47, 24.95, 25.23, 25.71, 26.16, 26.50, 27.31, 28.77, 29.44, 30.12, 30.37, 30.80, 31.93, 32.56, 33.34, 34.04, 35.06, 36.19, 37.45, 38.09, 38.89, 40.28, 43.04, 44.08, 44.96, 46.62, 47.34, 48.21, 48.75 and 49.36±0.2°.

Another aspect of the present invention provides a process for the preparation of crystalline bictegravir Form M1 comprising the steps of:
a) dissolving bictegravir sodium and fumaric acid in a mixture of water and organic solvent at elevated temperature;
b) cooling the reaction mass to 20-35° C.;
c) stirring the reaction mass to form the precipitation; and
d) isolating crystalline bictegravir Form M1.

According to the present disclosure, bictegravir sodium and fumaric acid are dissolved in a mixture of water and organic solvent at elevated temperature. The reaction mass is cooled and stirred to produce a solid. The obtained solid may then filtered and dried to get crystalline bictegravir Form M1.

Within the context of the present disclosure, bictegravir sodium and fumaric acid are dissolved in a mixture of water and organic solvent at elevated temperature, preferably of about 80-90° C.

Within the context of this embodiment of the present invention, the organic solvent employed may include, polar aprotic solvents such as dimethylformamide, dimethyl sulfoxide, dimethylacetamide or mixtures thereof. In particular useful embodiments of the present invention organic solvent is dimethyl sulfoxide.

Within the context of this embodiment of the present invention, isolation can be done using any techniques in the art such as, decantation, filtration by gravity or suction, centrifugation, slow evaporation, distillation. In particular useful embodiments of the present invention the solid is isolated by filtration followed by washing and drying.

In another aspect, the present invention provides crystalline bictegravir Form M2.

Within the context of the present invention, crystalline bictegravir Form M2 may be characterized by a PXRD pattern having significant peaks at 2θ angle positions at about 5.27, 10.54, 14.25 and 15.83±0.2°. In another embodiments, crystalline bictegravir Form M2 may be characterized by a PXRD pattern having significant peaks at 2θ angle positions at about 5.27, 5.64, 9.92, 10.54, 10.93, 12.42, 12.94, 14.25, 15.83, 16.30, 17.28, 17.62, 17.87, 18.53, 18.84, 19.38, 20.10, 20.86, 21.20, 21.63, 21.96, 23.36, 24.07, 24.50, 25.27, 25.75, 26.20, 26.54, 27.33, 28.64, 29.48, 30.16, 30.43, 30.84, 31.98, 32.62, 33.40, 34.06, 35.10, 36.31, 37.49, 38.12, 38.93, 40.31, 43.08, 44.11, 44.97, 47.37, 48.80 and 49.37±0.2°.

Another aspect of the present invention provides a process for the preparation of crystalline bictegravir Form M2 comprising the steps of:
a) dissolving bictegravir sodium and succinic acid in a mixture of water and organic solvent at elevated temperature;
b) cooling the reaction mass to 20-35° C.;
c) stirring the reaction mass to form the precipitation; and
d) isolating crystalline bictegravir Form M2.

According to the present disclosure, bictegravir sodium and succinic acid are dissolved in a mixture of water and organic solvent at elevated temperature. The reaction mass is cooled and stirred to produce a solid. The obtained solid may then filtered and dried to get crystalline bictegravir Form M2.

Within the context of the present disclosure, bictegravir sodium and succinic acid are dissolved in a mixture of water and organic solvent at elevated temperature, preferably of about 80-90° C.

Within the context of this embodiment of the present invention, the organic solvent employed may include, polar aprotic solvents such as dimethylformamide, dimethyl sulfoxide, dimethylacetamide or mixtures thereof. In particular useful embodiments of the present invention organic solvent is dimethyl sulfoxide.

Within the context of this embodiment of the present invention, isolation can be done using any techniques in the art such as, decantation, filtration by gravity or suction, centrifugation, slow evaporation, distillation. In particular useful embodiments of the present invention the solid is isolated by filtration followed by washing and drying.

In another aspect the present invention provides crystalline bictegravir Form M3.

Within the context of the present invention, crystalline bictegravir Form M3 may be characterized by a PXRD pattern having significant peaks at 2θ angle positions at about 5.25, 10.50, 14.22 and 16.47±0.2°. In another embodiments, crystalline bictegravir Form M3 may be characterized by a PXRD pattern having significant peaks at 2θ angle positions at about 5.25, 6.52, 9.89, 10.50, 10.78, 12.35, 12.99, 13.48, 13.77, 14.22, 14.64, 15.80, 16.13, 16.47, 16.80, 17.26, 17.85, 18.53, 18.93, 19.35, 20.07, 20.49, 20.85, 21.26, 21.46, 21.93, 22.46, 23.10, 23.36, 23.69, 24.05, 24.48, 24.85, 25.27, 25.56, 26.19, 26.59, 27.23, 28.22, 29.57, 30.36, 30.83, 31.21, 31.52, 31.95, 32.81, 34.06, 35.15, 35.74, 36.74, 37.46, 38.08, 38.42, 38.92, 39.61, 40.31, 41.50, 42.46, 43.06, 44.06, 45.04, 46.74, 47.35, 48.30 and 48.78±0.2°.

Another aspect of the present invention provides a process for the preparation of crystalline bictegravir Form M3 comprising the steps of:
a) dissolving bictegravir sodium and oxalic acid in a mixture of water and polar aprotic solvent at elevated temperature;
b) cooling the reaction mass to 20-35° C.;
c) stirring the reaction mass to form the precipitation; and
d) isolating crystalline bictegravir Form M3.

According to the present disclosure, bictegravir sodium and oxalic acid are dissolved in a mixture of water and polar aprotic solvent at elevated temperature. The reaction mass is cooled and stirred to produce a solid. The obtained solid may then filtered and dried to get crystalline bictegravir Form M3.

Within the context of the present disclosure, bictegravir sodium and oxalic acid are dissolved in a mixture of water and organic solvent at elevated temperature, preferably of about 80-90° C.

Within the context of this embodiment of the present invention, the polar aprotic solvent employed may include, dimethylformamide, dimethyl sulfoxide, dimethylacetamide or mixtures thereof. In particular useful embodiments of the present invention organic solvent is dimethyl sulfoxide.

Within the context of this embodiment of the present invention, isolation can be done using any techniques in the art such as, decantation, filtration by gravity or suction, centrifugation, slow evaporation, distillation. In particular useful embodiments of the present invention the solid is isolated by filtration followed by washing and drying.

In another aspect, the present invention provides crystalline bictegravir Form M4.

Within the context of the present invention, crystalline bictegravir Form M4 may be characterized by a PXRD pattern having significant peaks at 2θ angle positions at about 5.46, 6.07, 10.55 and 16.22±0.2°. In another embodiments, crystalline bictegravir Form M4 may be characterized by a PXRD pattern having significant peaks at 2θ angle positions at about 5.46, 6.07, 6.54, 6.99, 8.51, 10.03, 10.55, 10.87, 11.86, 12.33, 12.76, 13.11, 13.52, 14.24, 14.64, 14.95, 15.13, 15.45, 15.95, 16.22, 16.48, 17.07, 17.31, 17.66, 18.17, 18.64, 18.93, 19.22, 19.53, 19.89, 20.87, 21.46, 22.02, 22.26, 22.57, 23.10, 24.03, 24.56, 25.26, 25.73, 26.22, 26.80, 27.23, 27.52, 28.23, 28.97, 29.25, 29.57, 30.09, 30.76, 31.16, 32.66, 34.09, 35.33, 36.13, 36.79, 37.11, 38.90, 39.71, 40.28, 40.72, 41.52, 42.45, 43.12, 43.78, 44.52, 45.96, 46.61, 47.23 and 48.00±0.2°.

Another aspect of the present invention provides a process for the preparation of crystalline bictegravir Form M4 comprising the steps of:
a) dissolving bictegravir sodium and oxalic acid in a mixture of water and alcohol solvent at elevated temperature;
b) cooling the reaction mass to 20-35° C.;
c) stirring the reaction mass to form the precipitation; and
d) isolating crystalline bictegravir Form M4.

According to the present disclosure, bictegravir sodium and oxalic acid are dissolved in a mixture of water and alcohol solvent at elevated temperature. The reaction mass is cooled and stirred to produce a solid. The obtained solid may then filtered and dried to get crystalline bictegravir Form M4.

Within the context of the present disclosure, bictegravir sodium and oxalic acid are dissolved in a mixture of water and alcohol solvent at elevated temperature, preferably of about 80-90° C.

Within the context of this embodiment of the present invention, the alcohol solvent employed may include, methanol, ethanol, isopropanol or mixtures thereof. In particular useful embodiments of the present invention organic solvent is methanol.

Within the context of this embodiment of the present invention, isolation can be done using any techniques in the art such as, decantation, filtration by gravity or suction, centrifugation, slow evaporation, distillation. In particular useful embodiments of the present invention the solid is isolated by filtration followed by washing and drying.

In another aspect, the present invention provides crystalline bictegravir Form M5.

Within the context of the present invention, crystalline bictegravir Form M5 may be characterized by a PXRD pattern having significant peaks at 2θ angle positions at about 5.12, 6.33, 10.35 and 17.59±0.2°. In another embodiment, crystalline bictegravir Form M5 may be characterized by a PXRD pattern having significant peaks at 2θ angle positions at about 5.12, 6.33, 9.68, 10.35, 10.71, 12.74, 14.34, 16.57, 17.59, 18.55, 19.01, 19.81, 21.61, 23.05, 23.68, 24.13, 24.91, 25.81, 26.95, 27.74, 28.55, 31.67, 32.77, 35.68, 37.09 and 38.60±0.2°.

Another aspect of the present invention provides a process for the preparation of crystalline bictegravir Form M5 comprising drying the crystalline bictegravir Form M3 at 160-200° C.

In another aspect, the present invention provides amorphous bictegravir sodium.

Another aspect of the present invention provides a process for the preparation of amorphous bictegravir sodium, which comprises:
  a) dissolving bictegravir sodium in a solvent; and
  b) removing the solvent and isolating the amorphous bictegravir sodium.

Within the context of this embodiment of the present invention, the solvent employed may include, water and water miscible organic solvents such as acetone, acetonitrile 1,4-dioxane, tetrahydrofuran (THF), diglyme, methanol, ethanol, propanol, dimethyl formamide, ethylene glycol or mixtures thereof. In particular useful embodiments of the present invention solvent is a mixture of 1,4-dioxane and water or a mixture of acetonitrile and water or a mixture of THF and water.

Within the context of this embodiment of the present invention, removing of solvent can be done using any techniques in the art such as, decantation, filtration by gravity or suction, centrifugation, slow evaporation, distillation, lyophilization, spray drying. In particular useful embodiments of the present invention the solvent is removed by lyophilization or spray drying.

In another aspect the present invention is to provide amorphous solid dispersion of bictegravir sodium with pharmaceutically acceptable carriers.

Another aspect of the present invention is to provide a process for the preparation of amorphous solid dispersion of bictegravir sodium with pharmaceutically acceptable carriers, which comprises:
  a) dissolving bictegravir sodium in a solvent;
  b) adding pharmaceutically acceptable carrier to the solution obtained in step (a);
  c) removing the solvent and isolating the amorphous solid dispersion of bictegravir sodium.

Within the context of this embodiment of the present invention, the solvent employed may include, water and water miscible organic solvents such as acetone, acetonitrile 1,4-dioxane, diglyme, methanol, ethanol, propanol, dimethyl formamide, ethylene glycol or mixtures thereof. In particular useful embodiments of the present invention solvent is a mixture of 1,4-dioxane and water or a mixture of acetonitrile and water.

Within the context of this embodiment of the present invention, pharmaceutically acceptable carrier employed may include, povidone, copovidone, silicon dioxide, microcrystalline cellulose or mixtures thereof. Said povidone is selected from povidone K-17, povidone K-25, povidone K-30 and the like; said copovidone is selected from such as copovidones of which the brand names are Plasdone S-630 or Kollidon VA64 and the like. In particular useful embodiments of the present invention pharmaceutically acceptable carrier selected is silicon dioxide or microcrystalline cellulose.

Within the context of this embodiment of the present invention, removing of solvent can be done using any techniques in the art such as, decantation, filtration by gravity or suction, centrifugation, slow evaporation, distillation, lyophilization. In particular useful embodiments of the present invention the solvent is removed by lyophilization.

Another aspect of the present invention is to provide a process for the preparation of amorphous solid dispersion of bictegravir sodium with pharmaceutically acceptable carriers, which comprises:
  a) dissolving bictegravir sodium and pharmaceutically acceptable carrier in a solvent; and
  b) removing the solvent and isolating the amorphous solid dispersion of bictegravir sodium.

Within the context of this embodiment of the present invention, the solvent employed may include, water and water miscible organic solvents such as acetone, acetonitrile tetrahydrofuran (THF), diglyme, methanol, ethanol, propanol, dimethyl formamide, ethylene glycol or mixtures thereof. In particular useful embodiments of the present invention solvent is a mixture of THF and water.

Within the context of this embodiment of the present invention, pharmaceutically acceptable carrier employed may include, povidone, copovidone, silicon dioxide, hydroxypropyl methylcellulose (HPMC), microcrystalline cellulose or mixtures thereof. Said povidone is selected from povidone K-17, povidone K-25, povidone K-30 and the like; said copovidone is selected from such as copovidones of which the brand names are Plasdone S-630 or Kollidon VA64 and the like. In particular useful embodiments of the present invention pharmaceutically acceptable carrier selected is Plasdone S-630 or hydroxypropyl methylcellulose (HPMC).

Within the context of this embodiment of the present invention, removing of solvent can be done using any techniques in the art such as, spray drying, decantation, filtration by gravity or suction, centrifugation, slow evaporation, distillation. In particular useful embodiments of the present invention the solvent is removed by spray drying.

According to the present invention, the input bictegravir sodium is prepared by any prior-art process for example PCT publication No. WO2015196116A1.

Crystalline bictegravir Form M1, Form M2, amorphous form of bictegravir sodium and amorphous solid dispersion of bictegravir sodium with 50% Plasdone S-630 and 50% HPMC disclosed herein may exhibit enhanced stability during storage. Thus, the samples of crystalline bictegravir Form M1, Form M2, amorphous form of bictegravir sodium and amorphous solid dispersion of bictegravir sodium were stored at 40° C./75% relative humidity (RH) and at 25° C./60% relative humidity (RH) for 6 months. The samples were analyzed by PXRD for polymorph integrity.

Results of this testing revealed that crystalline bictegravir Form M1, Form M2 and amorphous bictegravir sodium shows no change in PXRD pattern and HPLC purity when stored for 6 months at 40° C. and 75% relative humidity (RH) and at 25° C. and 60% relative humidity (RH) conditions as mentioned in below Table 1.

TABLE 1

| Conditions/Polymorph | Bictegravir Form M1 | | Bictegravir Form M2 | | Bictegravir Sodium Amorphous form | |
|---|---|---|---|---|---|---|
| | PXRD | HPLC purity | PXRD | HPLC purity | PXRD | HPLC purity |
| at 40° C./75% RH | | | | | | |
| Initial | Crystalline | 99.66 | Crystalline | 99.68 | Amorphous from | 99.48 |
| 1 months | Stable | 99.67 | Stable | 99.67 | Stable | 99.68 |
| 2 months | Stable | 99.69 | Stable | 99.69 | Stable | 99.54 |
| 3 months | Stable | 99.80 | Stable | 99.73 | Stable | 99.48 |
| 6 months | Stable | 99.78 | Stable | 99.71 | Stable | 99.31 |
| at 25° C./60% RH | | | | | | |
| Initial | Crystalline | 99.66 | Crystalline | 99.68 | Amorphous from | 99.48 |
| 1 months | Stable | 99.68 | Stable | 99.68 | Stable | 99.68 |
| 2 months | Stable | 99.67 | Stable | 99.67 | Stable | 99.52 |
| 3 months | Stable | 99.73 | Stable | 99.73 | Stable | 99.54 |
| 6 months | Stable | 99.73 | Stable | 99.73 | Stable | 99.46 |

Amorphous solid dispersion of Bictegravir Sodium with 50% Plasdone S-630 shows no change in PXRD pattern and HPLC purity when stored for 6 months at 40° C. and 75% relative humidity (RH) and at 25° C. and 60% relative humidity (RH) conditions as mentioned in below Table 2.

TABLE 2

| Conditions/Polymorph | Amorphous solid dispersion of Bictegravir with 50% Plasdone S-630 | |
|---|---|---|
| | PXRD | HPLC purity |
| at 40° C./75% RH | | |
| Initial | Amorphous form | 99.44 |
| 1 months | Stable | 99.66 |
| 2 months | Stable | 99.52 |
| 3 months | Stable | 99.44 |
| 6 months | Stable | 99.43 |
| at 25° C./60% RH | | |
| Initial | Amorphous form | 99.44 |
| 1 months | Stable | 99.64 |
| 2 months | Stable | 99.51 |
| 3 months | Stable | 99.51 |
| 6 months | Stable | 99.44 |

Amorphous solid dispersion of Bictegravir Sodium with 50% HPMC shows no change in PXRD pattern and HPLC purity when stored for 3 months at 25° C. and 60% relative humidity (RH) condition as mentioned in below Table 3.

TABLE 3

| Conditions/Polymorph | Amorphous solid dispersion of Bictegravir Sodium with 50% HPMC | |
|---|---|---|
| | PXRD | HPLC purity |
| at 25° C./60% RH | | |
| Initial | Amorphous form | 99.39 |
| 1 months | Stable | 99.48 |
| 2 months | Stable | 99.41 |
| 3 months | Stable | 99.40 |

Certain specific aspects and embodiments of the present application will be explained in greater detail with reference to the following examples, which are provided only for purposes of illustration and should not be construed as limiting the scope of the disclosure in any manner. Reasonable variations of the described procedures are intended to be within the scope of the present application. While particular aspects of the present application have been illustrated and described, it would be apparent to those skilled in the art that various other changes and modifications can be made without departing from the spirit and scope of the disclosure. It is therefore intended to encompass all such changes and modifications that are within the scope of this disclosure.

EXAMPLES

Example 1

Preparation of Crystalline Bictegravir Form M1

Bictegravir Sodium (5 g) and fumaric acid (1.23 g) were dissolved in a mixture of dimethyl sulfoxide (60 mL) and water (20 mL) at 85±5° C. The reaction mass was cooled to 25±5° C. and maintained under stirring at 25±5° C. for 15 hours. The product obtained was filtered, washed with water (10 mL) and dried under vacuum at 50° C. for 13 hours. The solid obtained was identified as crystalline bictegravir Form M1.

Yield: 3.8 g

Example 2

Preparation of Crystalline Bictegravir Form M2

Bictegravir Sodium (5 g) and succinic acid (1.25 g) were dissolved in a mixture of dimethyl sulfoxide (62.5 mL) and water (25 mL) at 85±5° C. The reaction mass was cooled to 25±5° C. and maintained under stirring at 25±5° C. for 15 hours. The product obtained was filtered and dried under vacuum at 50° C. for 13 hours. The solid obtained was identified as crystalline bictegravir Form M2.

Yield: 3.8 g

Example 3

Preparation of Crystalline Bictegravir Form M3

Bictegravir Sodium (0.2 g) and oxalic acid (53.5 mg) were dissolved in a mixture of dimethyl sulfoxide (3 mL)

and water (1 mL) at 85±5° C. The reaction mass was cooled to 25±5° C. and maintained under stirring at 25±5° C. for 24 hours. The product obtained was filtered and suck-dried. The solid obtained was identified as crystalline bictegravir Form M3.

Yield: 0.15 g

Example 4

Preparation of Crystalline Bictegravir Form M4

Bictegravir Sodium (0.5 g) and oxalic acid (134 mg) were dissolved in a mixture of methanol (12.5 mL) and water (12.5 mL) at 80±5° C. The reaction mass was cooled to 25±5° C. and maintained under stirring for 24 hours. The product obtained was filtered and dried under vacuum at 50° C. for 2 hours. The solid obtained was identified as crystalline bictegravir Form M4.

Yield: 0.4 g

Example 5

Preparation of Crystalline Bictegravir Form M5

Bictegravir Form M3 (0.2 g) was heated up to 180° C. using variable temperature powder XRD tool on Bruker D8 X-Ray Diffractometer. The resulting solid was identified as crystalline bictegravir Form M5.

Example 6

Preparation of Amorphous Bictegravir Sodium

Bictegravir Sodium (0.25 g) was dissolved in a mixture of acetonitrile (30 mL) and water (30 mL) at 85±5° C. The resulting clear solution was filtered to remove any undissolved particulates and subjected to lyophilisation using Labocon lyophilizer to yield amorphous bictegravir sodium.

Example 7

Preparation of Amorphous Bictegravir Sodium

Bictegravir Sodium (0.25 g) was dissolved in a mixture of 1,4-dioxane (30 mL) and water (30 mL) at 85±5° C. The resulting clear solution was filtered to remove any undissolved particulates and subjected to lyophilisation using Labocon lyophilizer to yield amorphous bictegravir sodium.

Example 8

Preparation of Amorphous Bictegravir Sodium

Bictegravir Sodium (5 g) was dissolved in a mixture of tetrahydrofuran (350 mL) and water (150 mL) at 70±5° C. The resulting clear solution was filtered to remove any undissolved particulates and subjected to spray-drying in a laboratory spray-dryer (Model: Buchi B-290) with feed rate of solution 5 mL/min and inlet temperature at 80° C. with 100% aspiration to yield amorphous bictegravir sodium.

Example 9

Preparation of Amorphous Solid Dispersion of Bictegravir Sodium

Bictegravir Sodium (0.25 g) was dissolved in a mixture of 1,4-dioxane (28 mL) and water (25 mL) at 85±5° C. The resulting clear solution was filtered to remove any undissolved particulates and added Silicon dioxide (0.25 g) and subjected to lyophilisation using Labocon lyophilizer to yield amorphous solid dispersion of bictegravir sodium.

Example 10

Preparation of Amorphous Solid Dispersion of Bictegravir Sodium

Bictegravir Sodium (0.25 g) was dissolved in a mixture of acetonitrile (28 mL) and water (25 mL) at 85±5° C. The resulting clear solution was filtered to remove any undissolved particulates and added Silicon dioxide (0.25 g) and subjected to lyophilisation using Labocon lyophilizer to yield amorphous solid dispersion of bictegravir sodium.

Example 11

Preparation of Amorphous Solid Dispersion of Bictegravir Sodium

Bictegravir Sodium (0.25 g) was dissolved in a mixture of 1,4-dioxane (30 mL) and water (30 mL) at 85±5° C. The resulting clear solution was filtered to remove any undissolved particulates and added Microcrystalline cellulose (0.25 g) and subjected to Lyophilisation using Labocon lyophilizer to yield amorphous solid dispersion of bictegravir sodium.

Example 12

Preparation of Amorphous Solid Dispersion of Bictegravir Sodium

Bictegravir Sodium (0.25 g) was dissolved in a mixture of acetonitrile (30 mL) and water (30 mL) at 85±5° C. The resulting clear solution was filtered to remove any undissolved particulates and added Microcrystalline cellulose (0.25 g) and subjected to Lyophilisation using Labocon lyophilizer to yield amorphous solid dispersion of bictegravir sodium.

Example 13

Preparation of Amorphous Solid Dispersion of Bictegravir Sodium

Bictegravir Sodium (4 g) and Plasdone S-630 (4 g) were dissolved in a mixture of tetrahydrofuran (280 mL) and water (120 mL) at 70±5° C. The resulting clear solution was filtered to remove any undissolved particulates and subjected to spray-drying in a laboratory spray-dryer (Model: Buchi B-290) with feed rate of solution 5 mL/min and inlet temperature at 80° C. with 100% aspiration to yield amorphous solid dispersion of bictegravir sodium.

Example 14

Preparation of Amorphous Solid Dispersion of Bictegravir Sodium

Bictegravir Sodium (5 g) and HPMC (5 g) were dissolved in a mixture of tetrahydrofuran (370 mL) and water (140 mL) at 70±5° C. The resulting clear solution was filtered to remove any undissolved particulates and subjected to spray-drying in a laboratory spray-dryer (Model: Buchi B-290)

with feed rate of solution 5 mL/min and inlet temperature at 80° C. with 100% aspiration to yield amorphous solid dispersion of bictegravir sodium.

We claim:

1. A crystalline bictegravir Form M4, characterized by a powder X-ray diffraction pattern having significant peaks at 2Θ angles positions at about 10.96, 16.98, 20.15, 22.16 and 26.01±0.2°, measured with a Cu-anode X-ray tube operated at 40 kV and 30 mA.

2. A crystalline bictegravir Form M4, characterized by a PXRD pattern as shown in FIG. 4, measured with a Cu-anode X-ray tube operated at 40 kV and 30 mA.

3. A process for the preparation of crystalline bictegravir Form M4, comprising the steps of:
  a) dissolving bictegravir sodium and oxalic acid in a mixture of water and alcohol solvent at elevated temperature;
  b) cooling the reaction mass to 20-35 °C.;
  c) stirring the reaction mass to form the precipitation; and
  d) isolating crystalline bictegravir Form M4.

4. The process of claim 3, wherein the crystalline bictegravir Form M4 is characterized by a powder X-ray diffraction pattern having significant peaks at 2Θ angles positions at about 10.96, 16.98, 20.15, 22.16 and 26.01±0.2°, measured with a Cu-anode X-ray tube operated at 40 kV and 30 mA.

5. The process of claim 3, wherein the crystalline bictegravir Form M4 is characterized by a PXRD pattern as shown in FIG. 4, measured with a Cu-anode X-ray tube operated at 40 kV and 30 mA.

* * * * *